US00PP25982P3

(12) United States Plant Patent
Lugli et al.

(10) Patent No.: US PP25,982 P3
(45) Date of Patent: Oct. 13, 2015

(54) CHERRY TREE NAMED 'PA2UNIBO'

(50) Latin Name: *Prunus avium*
Varietal Denomination: PA2UNIBO

(71) Applicant: Alma Mater Studiorum-Università degli Studi di Bologna, Bologna (IT)

(72) Inventors: Stefano Lugli, Modena (IT); Riccardo Correale, Bologna (IT); Michelangelo Grandi, Castenaso (IT)

(73) Assignee: Alma Mater Studiorum-Università degli Studi di Bologna, Bologna (IT)

( * ) Notice: Subject to any disclaimer, the term of this patent is extended or adjusted under 35 U.S.C. 154(b) by 117 days.

(21) Appl. No.: 13/986,701

(22) Filed: May 28, 2013

(65) Prior Publication Data

US 2013/0326771 P1 Dec. 5, 2013

(30) Foreign Application Priority Data

May 25, 2012 (EP) ..... 2012/1158

(51) Int. Cl.
*A01H 5/00* (2006.01)
*A01H 5/08* (2006.01)

(52) U.S. Cl.
USPC ..... Plt./181
CPC ..... *A01H 5/085* (2013.01)

(58) Field of Classification Search
USPC ..... Plt./181
See application file for complete search history.

(56) References Cited

PUBLICATIONS

PLUTO Plant Variety Database Dec. 2014.*

* cited by examiner

*Primary Examiner* — Annette Para
(74) *Attorney, Agent, or Firm* — Hershkovitz & Associates, PLLC; Abraham Hershkovitz

(57) ABSTRACT

'PA2UNIBO' is a novel cherry tree of the genus/species *Prunus avium* derived from a seedling of unknown cross which was planted at Vignola, Modena Province, Italy. It was initially propagated by grafting to root stocks of varying vigor and, after testing in districts and plantings of differing types, proved to have the qualities proper to a promising new cultivar for the market.

5 Drawing Sheets

Latin name of the genus/species of the plant claimed (cultivar): *Prunus avium.*

Variety denomination: PA2UNIBO.

CROSS-REFERENCE TO RELATED APPLICATIONS

This application claims priority of pending EU Plant Patent for 'PA2UNIBO', which was filed on 25 May 2012 as Application No. 2012/1158 in the name of Applicant (holder) Alma Mater Studiorum—Università degli Studi di Bologna, the entire contents of which is expressly incorporated herein by reference. EU Trademark for 'Sweet Lorenz' was released on 2 Jan. 2013 as Registration No. 011043973 of Applicant (holder) Alma Mater Studiorum—Università degli Studi di Bologna. Such European Trademark is associated to PA2UNIBO and used to distinguish such cherry variety from the others.

FIELD OF THE INVENTION

*Prunus avium* 'PA2UNIBO' is derived from a seedling of unknown cross and originally called DCA BO A1C27. It was planted at Vignola, Modena Province, Italy, in February 2002 and first cropped in 2004. It was initially propagated by grafting to root stocks of varying vigor, tested in different growing districts and planting densities and proved to have the properties proper to a promising new cultivar for the market. It picks in the end of May to the middle of June in Modena Province, about 10 days after 'Burlat' or about 8 days before 'Bing', and at about the same date as 'Celeste'® (Sumpaca*).

SUMMARY OF THE INVENTION

The parentage of the variety is unknown. The name of a comparison variety is 'Celeste'® (Sumpaca*). However, compared to 'Celeste'® (Sumpaca*), 'PA2UNIBO' has larger (30 mm caliber prevalent), firmer fruit of more uniform ripening and higher sugar content. 'PA2UNIBO' was selected for its high qualities, including tree growth and yield performance, fruit appearance and excellent taste-flavor properties, very sweet and with a good level of acidity. Its distinctive traits include early-mid season picking, uniform maturing and large-sized fruit of firm flesh, with an excellent stability of maturation guaranteeing over 15 days picking. The date of cross was in the year 2000. The location of the discovery was Vignola, Modena Province, Italy. The date of the first asexual propagation was in 2008 in Vignola, Modena Province, Italy. 'PA2UNIBO' resulted from a cross of unknown varieties, but was originally propagated on 'Colt' (U.S. Plant Pat. No. 4,059) and 'Gisela 6' (U.S. Plant Pat. No. 8,954) root stocks of differing vigor in trial fields of Bologna University to test growth and yield performance under different planting systems.

BRIEF DESCRIPTION OF THE DRAWINGS

The accompanying photographs show typical specimens of the new variety as depicted in color as nearly true as is reasonably possible in color illustrations of this character.

DETAILED BOTANICAL DESCRIPTION OF THE VARIETY

Figure 1:
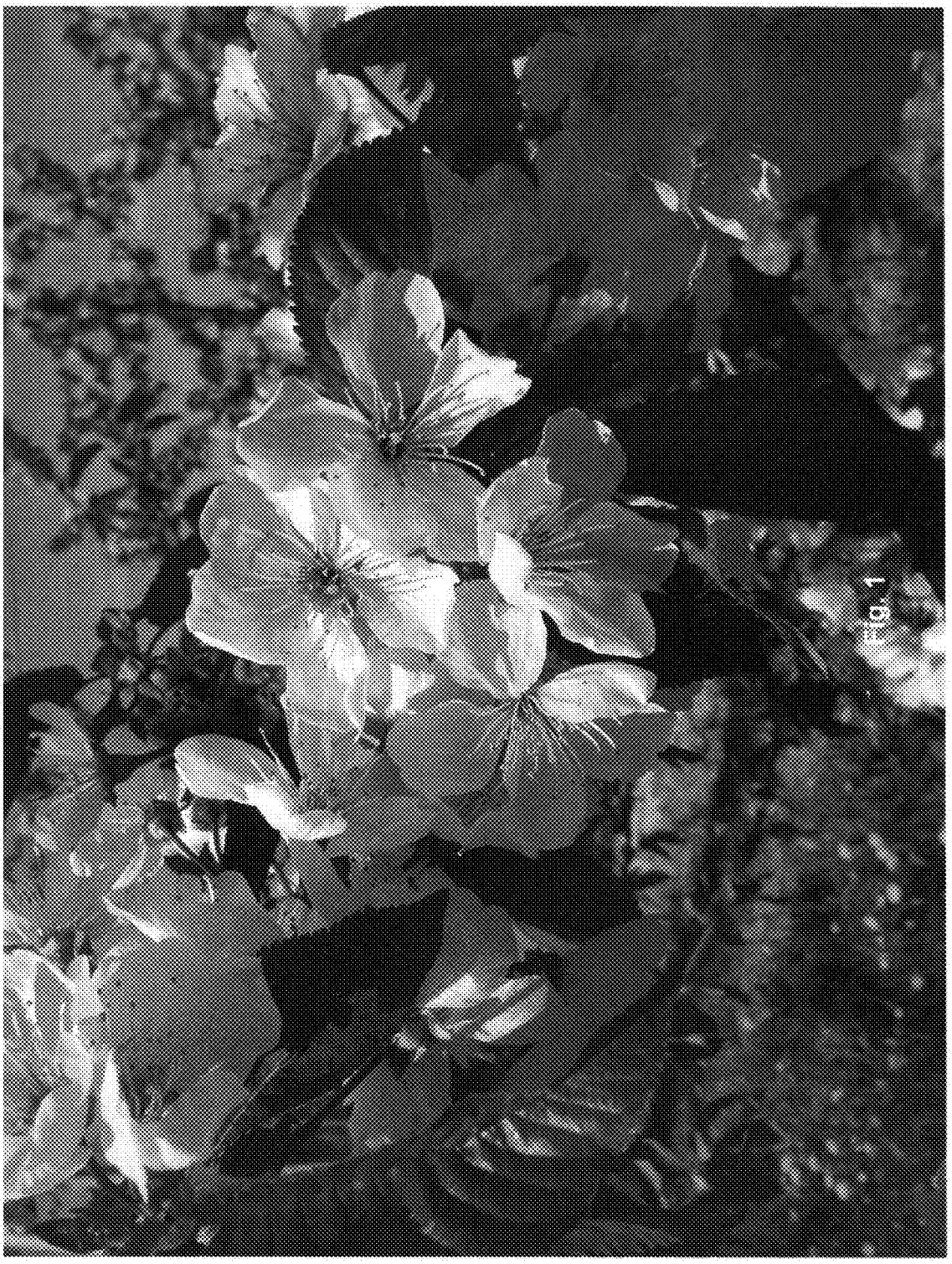
FIG. 1 illustrates the detail of fully-open blossoms of PA2UNIBO.
Figure 2:
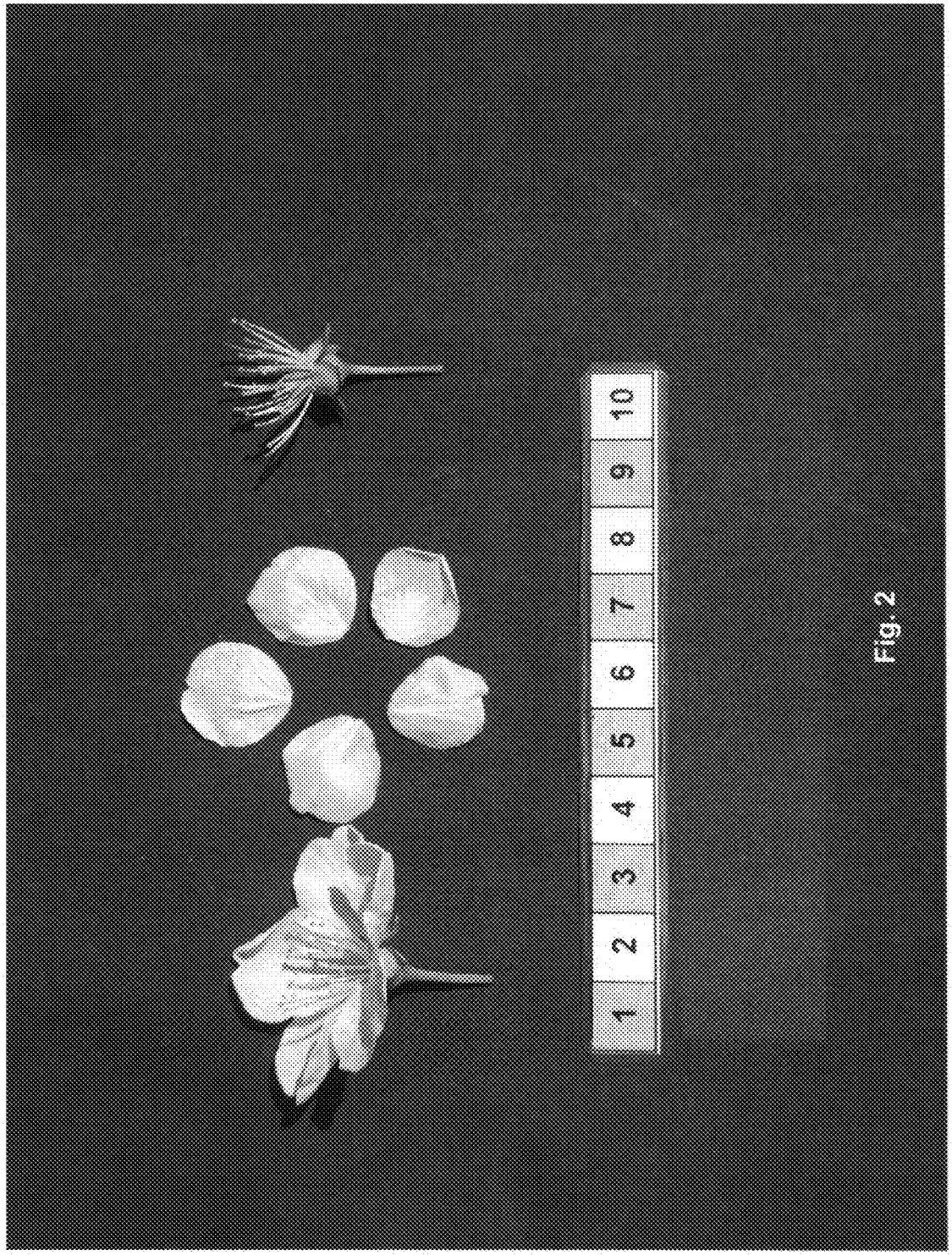
FIG. 2 shows the flower, full front, in profile and with separated petals, of PA2UNIBO.
Figure 3:
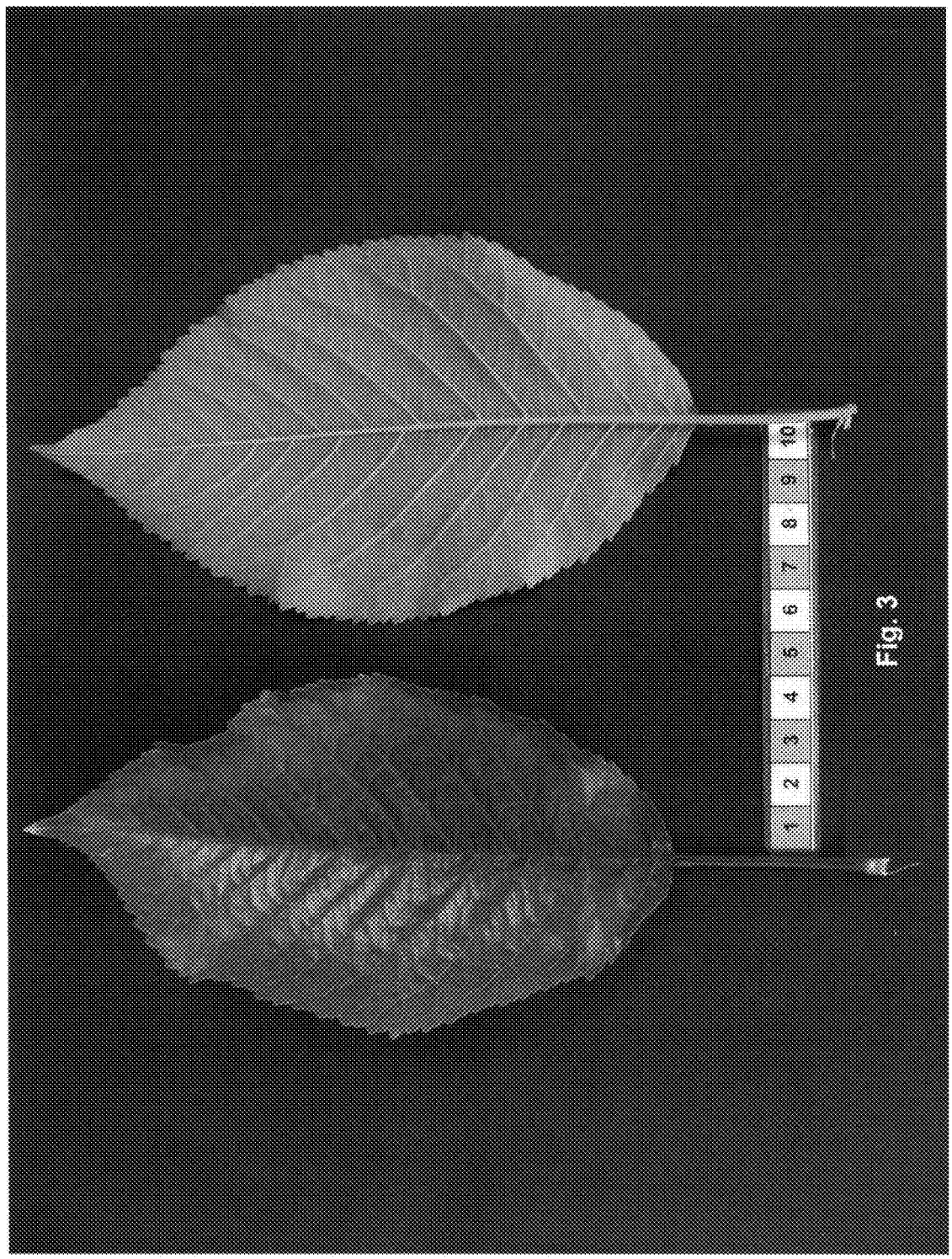
FIG. 3 3 shows the leaf profile of PA2UNIBO. Two leaves have been detached and one has been placed upper leaf surface side down to show the lower leaf surface details.
Figure 4:
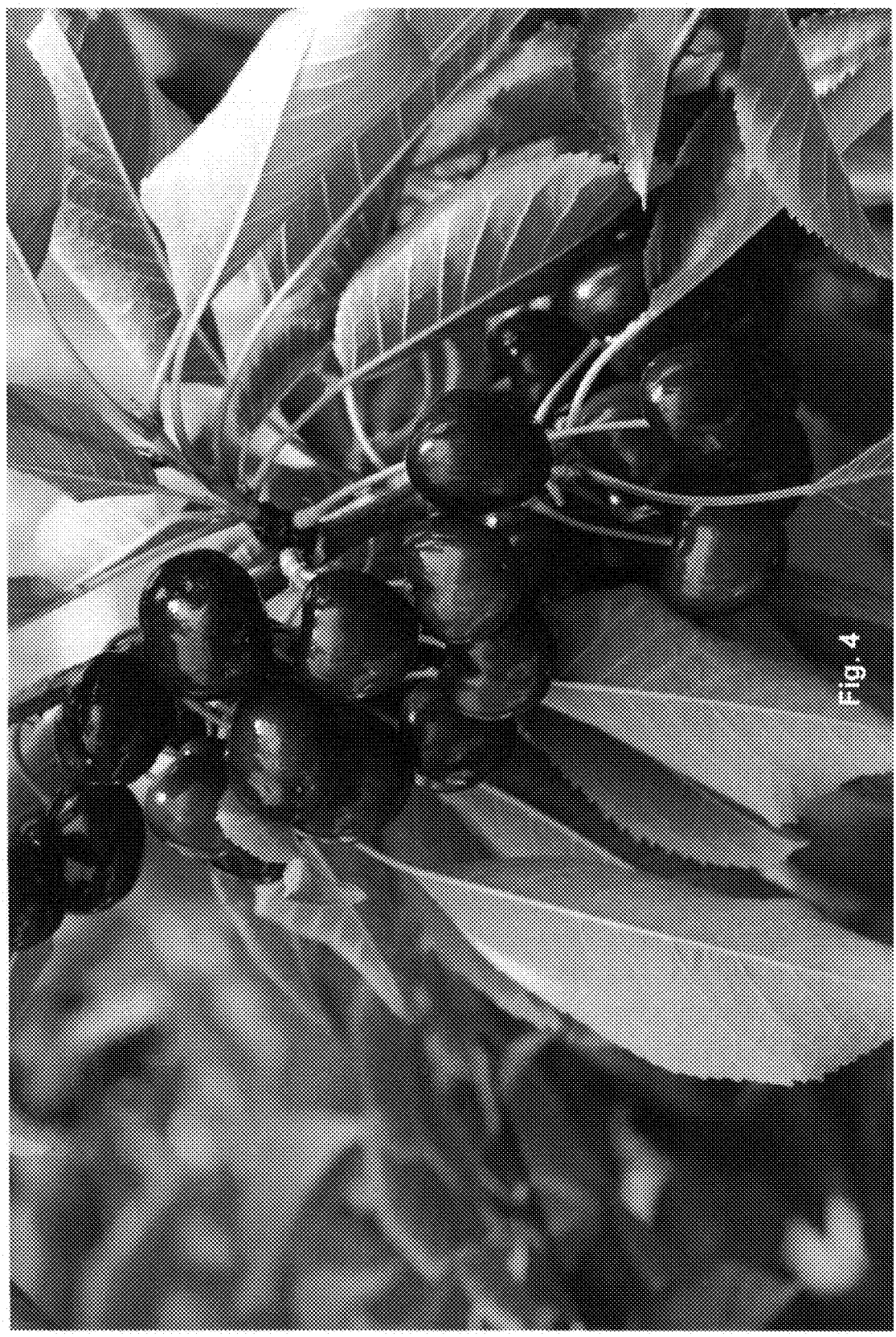
FIG. 4 shows details of fruit cropping of PA2UNIBO.
Figure 5:
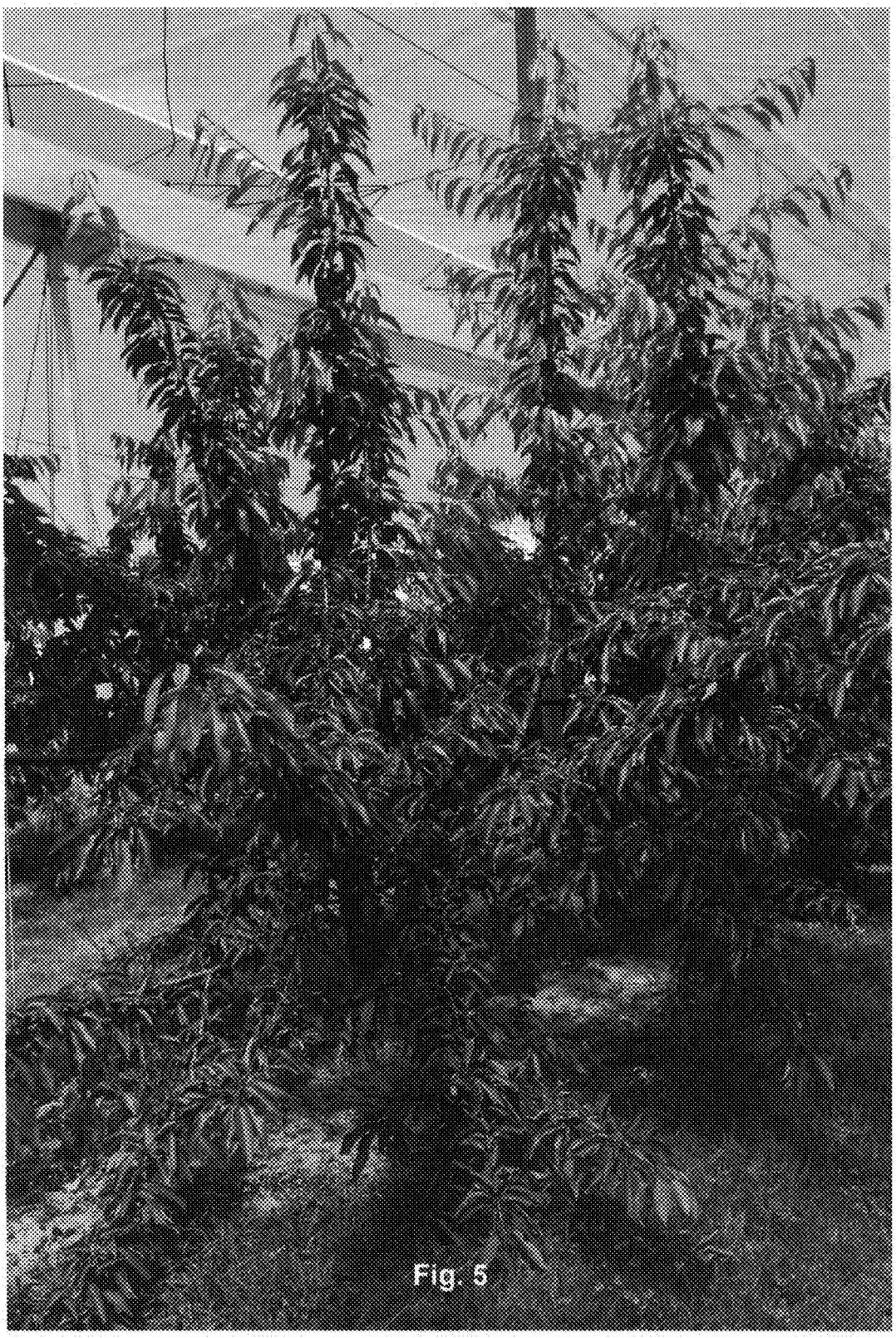
FIG. 5 shows the tree habit, with width-spread and height, of PA2UNIBO.

General:
- *Age of described tree(s).*—5 years, multi-leader spindle training system.
- *Location of described trees(s).*—Vignola, Modena Province, Italy.
- *Name of color chart used.*—Royal Horticultural Society Colour Chart.
- *Name of root stock.*—'Colt'.

Tree:
- *Vigor.*—High.
- *Height.*—4-4.5 meters.
- *Spread.*—3 meters.
- *Growth habit.*—Semi-open.
- *Canopy density.*—Medium.
- *Trunk diameter at specified height.*—18-22 cm, as measured about 5 cm above graft joint.
- *Trunk color.*—Grayish (201A) with reddish nuances (183A).
- *Bark texture.*—Of average roughness.
- *Tendency toward alternate bearing.*—No.
- *Winter hardiness.*—Unknown, no winter cold damage found in this Po Valley district.
- *Chilling requirement.*—Unknown.

Branch:
- *Length.*—300-400 cm.
- *Diameter.*—5-6 cm.
- *Crotch angle.*—50°-60° depending on training system.
- *Bark color.*—Reddish-brown (200C) with widespread gray overtone (201A).
- *Bark texture.*—Of medium fineness.

Current year shoot:
- *Length.*—35-50 cm.
- *Color.*—Reddish-brown (200C/200D) with widespread gray overtone (201A).

Winter hardiness:
- *USDA hardiness zone.*—Unknown.
- *Chilling requirement.*—Unknown.

Flower buds:
- *Number per spur.*—5-6.
- *Shape.*—Sub-globose.
- *Length.*—About 1 cm.
- *Diameter.*—Under 1 cm.
- *Color.*—Reddish perules (187C).

Flowers:
- *Number per cluster.*—Minimum 6-maximum 9 per spur; 2-3 per bud. Abundant bloom.
- *Relative position of petals.*—Slightly overlapping petals.
- *Diameter.*—35-42 mm.
- *Depth.*—15-18 mm, measured as distance from receptacle to maximum petal aperture.
- *Is pollen produced?.*—Yes.
- *Coloration of pollen.*—Yellow (13A).

Sepal:
- *Length.*—6-8 mm.
- *Shape.*—Conical.
- *Width.*—5-6 mm.
- *Apex.*—Pointed.
- *Base.*—Pointed.
- *Margin descriptors.*—Regular margin.
- *Color—upper surface.*—Pale green (138C).
- *Color—lower surface.*—Pale green (138C).

Petals:
- *Number per flower.*—5.
- *Shape.*—Circular.
- *Length.*—16-20 mm.
- *Width.*—16-20 mm.
- *Apex.*—Slightly sunken.
- *Base.*—Slightly pointed.
- *Margin.*—Slightly undulated.
- *Color—upper surface.*—White (155B).
- *Color—lower surface.*—White (155B).

Bloom:
- *Date of bud burst.*—7-8 Apr. 2013.
- *Date of first bloom.*—13 Apr. 2013.
- *Date of full bloom.*—16 Apr. 2013.

Pedicel:
- *Length.*—33-36 mm.
- *Diameter.*—About 1.1 mm.
- *Color.*—Green (143B).

Pistil:
- *Quantity.*—1.
- *Size.*—18-21 mm.
- *Color.*—Green (143C).

Anthers:
- *Quantity.*—24-28: about 70% are 10-13 mm long, positioned slightly under the top of the stigma, and 1-2 anthers of many flowers are longer than the top of the stigma. The remaining 30% are 5-8 mm long. White filament (155D).
- *Size.*—About 1 mm in diameter.
- *Color.*—Yellow (15C).

Stigma:
- *Quantity.*—1.
- *Size.*—1.2-1.3 mm in diameter.
- *Color.*—Green (142A).

Styles:
- *Quantity.*—1.
- *Size.*—14-15 mm long.
- *Color.*—Pale green (142B) turning to rosè (36C) at end of bloom.

Ovary/ies:
- *Quantity.*—1.
- *Size.*—4-5 mm.
- *Color.*—Green (143C).

Leaves:

*Length.*—14.1-15.2 cm.
*Width.*—7.8-8.8 cm.
*Shape.*—Elliptical.
*Apex shape.*—Pointed.
*Base shape.*—Pointed.
*Margin.*—Fine-toothed.
*Color—upper surface.*—Dark green (137A).
*Color—lower surface.*—Pale green (138A/138B) with green-yellow central vein (152A/152B).

Petiole:

*Length.*—4-4.8 cm.
*Diameter.*—About 2 mm.
*Color.*—Green-yellow (152A/152B) under and reddish upper (183A).

Fruit:

*Shape.*—Heart-shaped.
*Diameter.*—Mostly 30 mm.
*Height.*—24-27 mm.
*Weight.*—12-14 g, average weight.
*Number per cluster.*—5-8 per spur.
*Skin color* (*include ground color and over color*).—Shiny dark red (187B) tending oward blackish dark red (187A) at advanced maturity.
*Presence of lenticels.*—Yes.
*Density of lenticels.*—Medium.
*Skin thickness.*—Medium.
*Skin texture.*—Medium.
*Anthocyanin coloration present near skin?.*—No.
*Tenacity of flesh to stone.*—Low.
*Flesh color.*—Rosé (52A).
*Flesh texture.*—Fine.
*Juiciness.*—High.
*Juice analysis* (*brix, acidity, tss, etc.*).—18.2° Brix and 8.3 g/l malic acid (2012 data).
*Stone size.*—Medium-small.
*Stone shape.*—Elliptical.
*Stone color.*—Pale brown (165D).

Fruit stem:

*Length.*—35-38 mm.
*Diameter.*—Over 1 mm.
*Color.*—Green (143B).

Harvest:

*Maturity date range.*—May 25-June 15, approximately 10 days after 'Burlat' or about 8 days before 'Bing', and at about the same date as 'Celeste'® (Sumpaca*). Optimum harvest dates for 'PA2UNIBO' in Modena Province are May 30-June 7.
*Harvest date range* (*if different*).—Same as above.

The diploid 'PA2UNIBO' is not self-fertile (with an allelic profile of S3S4), and requires pollinators for optimum fruit load and yield. Pollinators include Sweet Aryana® 'PA1UNIBO' (U.S. Plant patent application Ser. No. 13/986,702), Sweet Gabriel® 'PA3UNIBO' (U.S. Plant patent application Ser. No. 13/986,703) and Sweet Saretta® 'PA5UNIBO' (U.S. Plant patent application Ser. No. 13/896,686), although other same-species pollinators are anticipated to be compatible and prove productive.

Under observation during planting, growing and harvesting under normal cultural and growing conditions in Modena Province, Italy, no particular inset or plant/fruit disease resistance or susceptibility has been observed.

Because of the outstanding and unique horticultural characters of the claimed plant, especially its long harvest period and large size, this cherry can be planted to extend the cultivar's season. Although this new variety of cherry possesses the above-described characteristics, it is to be understood that variations and fluctuations may occur in the magnitude and qualities due to changes in growing and climate conditions, irrigation, fertilization, pruning and pest control.

What is claimed is:

1. A new and distinct cherry tree as herein described and illustrated.

* * * * *